US011045085B2

(12) United States Patent
Nauche et al.

(10) Patent No.: US 11,045,085 B2
(45) Date of Patent: Jun. 29, 2021

(54) OPTOMETRY DEVICE AND METHOD OF PERFORMING A TEST USING SUCH AN OPTOMETRY DEVICE

(71) Applicant: Essilor International, Charenton-le-Pont (FR)

(72) Inventors: Michel Nauche, Charenton-le-Pont (FR); Stéphane Boutinon, Charenton-le-Pont (FR); Vincent Tejedor Del Rio, Charenton-le-Pont (FR); Joel Batisse, Charenton-le-Pont (FR); Christophe Condat, Charenton-le-Pont (FR); Pierre Rolland, Charenton-le-Pont (FR); Didier Grand-Clement, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 119 days.

(21) Appl. No.: 16/335,493

(22) PCT Filed: Sep. 20, 2017

(86) PCT No.: PCT/EP2017/073820
§ 371 (c)(1),
(2) Date: Mar. 21, 2019

(87) PCT Pub. No.: WO2018/055000
PCT Pub. Date: Mar. 29, 2018

(65) Prior Publication Data
US 2020/0015672 A1 Jan. 16, 2020

(30) Foreign Application Priority Data
Sep. 22, 2016 (EP) .................................. 16306223

(51) Int. Cl.
*A61B 3/032* (2006.01)
*A61B 3/00* (2006.01)
*A61B 3/06* (2006.01)

(52) U.S. Cl.
CPC ............ *A61B 3/032* (2013.01); *A61B 3/0008* (2013.01); *A61B 3/0016* (2013.01); *A61B 3/063* (2013.01)

(58) Field of Classification Search
CPC .................................................... A61B 3/032
(Continued)

(56) References Cited

U.S. PATENT DOCUMENTS 5,550,602 A * 8/1996 Braeuning ............. A61B 3/024
351/243
10,194,795 B2 2/2019 Nauche et al.
(Continued)

FOREIGN PATENT DOCUMENTS

CN 1498090 A 5/2004
CN 2824835 Y 10/2006
(Continued)

OTHER PUBLICATIONS

International Search Report, dated Feb. 22, 2018, from corresponding PCT application.
(Continued)

*Primary Examiner* — James C. Jones
(74) *Attorney, Agent, or Firm* — Nixon & Vanderhye

(57) ABSTRACT

An optometry device for testing an individual's eye includes: a casing; an imaging module located in the casing and adapted to produce a light beam directed to the individual's eye; and a refraction module adapted to provide a variable optical correction to the individual's eye looking there through into the casing. The optometry device includes
(Continued)

an illumination system adapted to produce a variable ambient light level inside the casing.

18 Claims, 3 Drawing Sheets

(58) Field of Classification Search
USPC .......................................................... 351/246
See application file for complete search history.

(56) References Cited

U.S. PATENT DOCUMENTS

| | | |
|---|---|---|
| 2002/0047997 A1 | 4/2002 | Hayashi et al. |
| 2004/0095556 A1 | 5/2004 | Mihashi et al. |
| 2008/0246921 A1 | 10/2008 | Mihashi et al. |
| 2009/0073386 A1 | 3/2009 | Petito et al. |
| 2009/0153796 A1 | 6/2009 | Rabner |
| 2013/0027668 A1 | 1/2013 | Pamplona et al. |
| 2016/0331226 A1 | 11/2016 | Nauche et al. |
| 2017/0035289 A1 | 2/2017 | Boutinon et al. |

FOREIGN PATENT DOCUMENTS

| | | |
|---|---|---|
| CN | 101716067 A | 6/2010 |
| CN | 204683563 U | 10/2015 |
| CN | 105662800 A | 6/2016 |
| CN | 205458596 U | 8/2016 |
| DE | 30 03 588 A1 | 8/1981 |
| WO | 2015/092233 A1 | 6/2015 |
| WO | 2015/107303 A1 | 7/2015 |

OTHER PUBLICATIONS

Office Action issued in Chinese Patent Application No. 201780058092.0 dated Feb. 3, 2021.

* cited by examiner

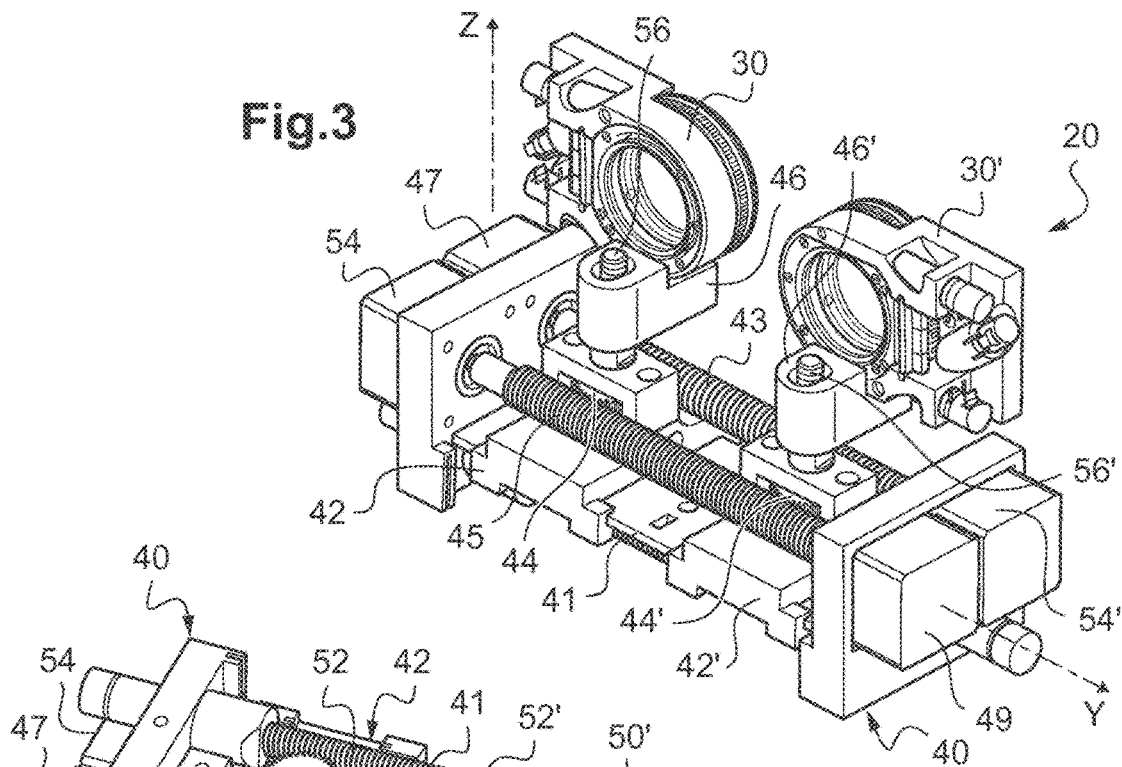
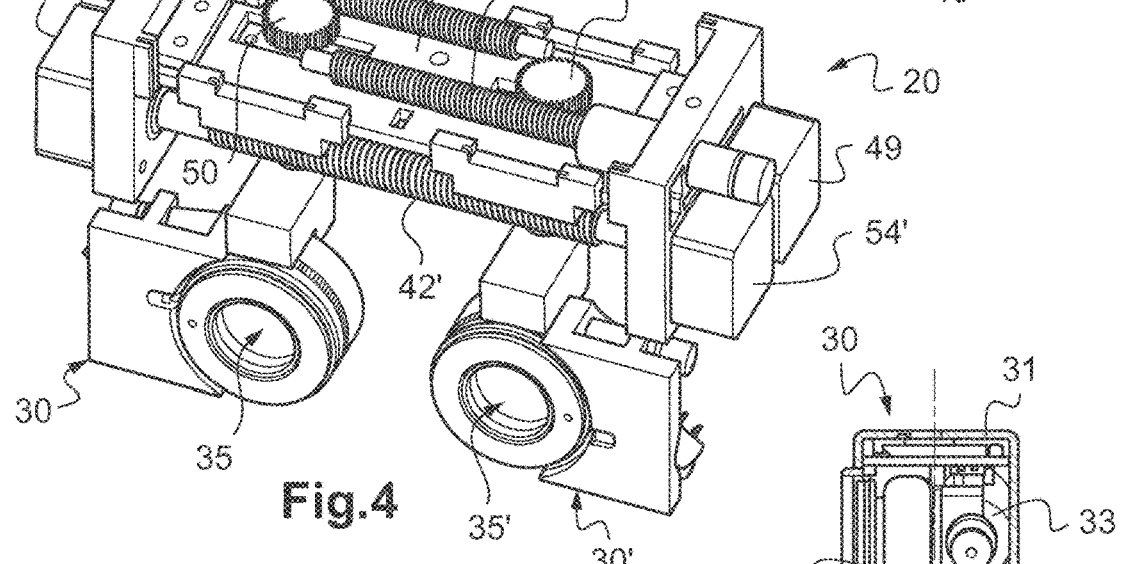
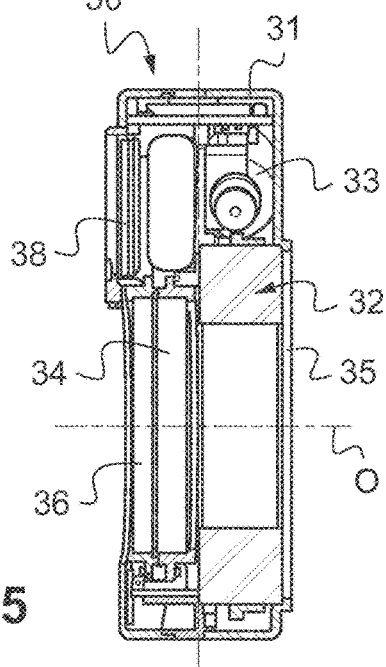

OPTOMETRY DEVICE AND METHOD OF PERFORMING A TEST USING SUCH AN OPTOMETRY DEVICE

TECHNICAL FIELD OF THE INVENTION

The invention relates to the field of optometry.

More precisely the invention relates to an optometry device and to a method of performing a test using such an optometry device.

BACKGROUND INFORMATION AND PRIOR ART

Optometry devices are used by eye care professionals, in particular optometrists and ophthalmologists, to assist them in assessing characteristics of an individual's vision.

In particular, a refraction apparatus is an optometry device adapted to generate a variable correction and used during a test known as "subjective refraction" in order to determine the necessary correction for compensating an individual's ametropia.

Such a test is performed with the ambient light of the room used for the test and thus for only one type of vision, generally photopic vision.

SUMMARY OF THE INVENTION

The invention provides an optometry device for testing an individual's eye comprising a casing, an imaging module located in the casing and adapted to produce a light beam directed to the individual's eye, and a refraction module adapted to provide a variable optical correction to the individual's eye looking therethrough into the casing, characterised by an illumination system adapted to produce a variable ambient light level inside the casing.

Such an optometry device makes it possible to perform a subjective refraction test for various types of vision, depending on the ambient light level chosen (e.g. by the eye care practitioner) during the test.

The optometry device may also include one or several of the following optional features (which are to be understood as non limiting):
- the illumination system includes at least one surface and one light source located around the imaging module;
- the refraction module is displaceably mounted between a first position, in which first position the refraction module is crossed by the light beam, and a second position, in which second position the refraction module is retracted out of the light beam;
- the imaging module is designed to project the light beam through an eyepiece of the refraction module when the refraction module is in the first position;
- the refraction module is mounted on a carriage having a gear cooperating with two parallel worms respectively driven by two motors;
- the refraction module is mounted on the carriage at a position adjustable along a direction perpendicular to an optical axis of the refraction module;
- the refraction module includes a lens with variable spherical refraction power;
- the variable refraction module includes a pair of independently rotatable lenses with cylindrical refraction power;
- the light beam is designed to form to an optotype for the individual's eye.

The invention also provides a method of performing a test using an optometry device as mentioned above, including a step of varying said ambient light level during the test.

BRIEF DESCRIPTION OF THE DRAWINGS

The following description will be made in light of the appended figures, where:

FIG. 3 is a first perspective view of a refraction unit of the optometry device of FIG. 1;

FIG. 4 is a second perspective view of a refraction unit of the optometry device of FIG. 1;

FIG. 5 shows a possible embodiment for refraction modules provided in such an optometry device;

DETAILED DESCRIPTION OF EXAMPLE(S)

Figure 1:
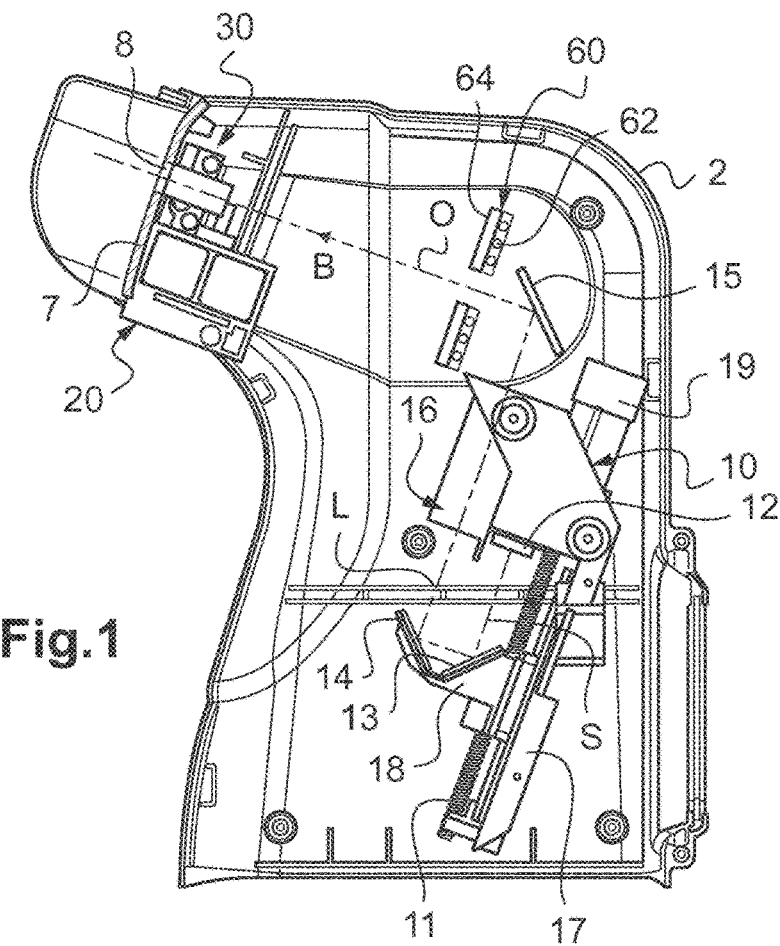
FIG. 1 shows a first embodiment of an optometry device according to the invention.
Figure 2:
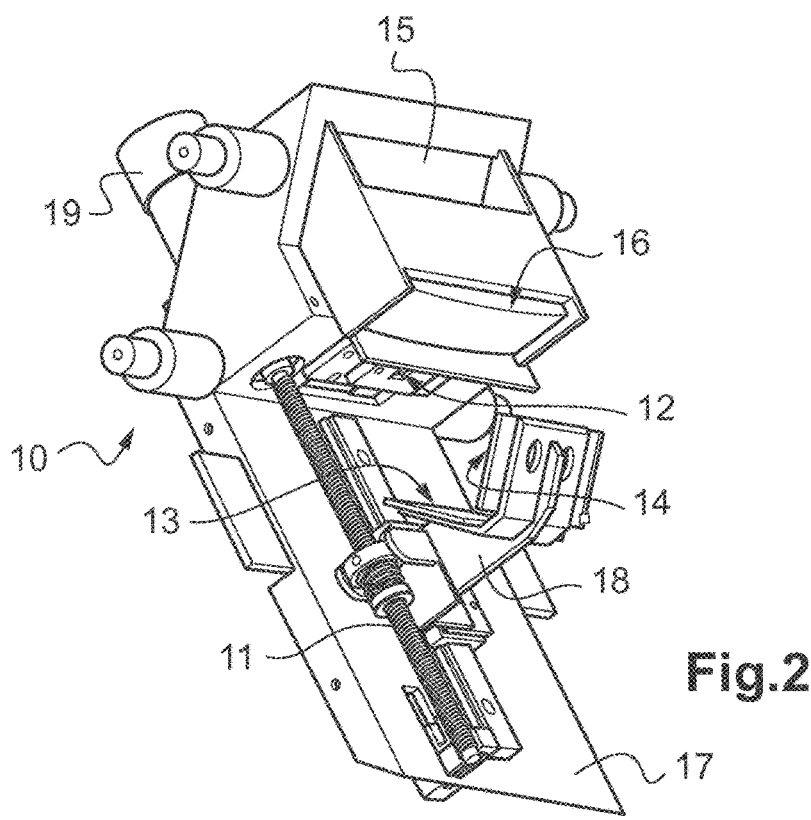
FIG. 2 is a perspective view of an imaging module of the optometry device of FIG. 1.

The optometry device of FIG. 1 includes a casing 2 enclosing an imaging module 10, a refraction unit 20 and an illumination system 60.

As will be further explained below, the refraction unit 20 includes two refraction modules 30, 30' and a driving module 40.

The casing 2 includes a wall 7 situated opposite the imaging module 10 and having windows 8 (possibly closed by a transparent material, such as a transparent plastic) through which an individual can look into the casing 2, as further explained below.

The imaging module 10 includes a screen 12, a pair of mirrors 13, 14, a lens 16 and a further mirror 15.

The screen 12 (for instance an LCD screen) produces a light beam along a screen axis S (this screen axis S being almost vertical in the present case). As further explained below, this light beam is meant to produce an image of an object, such as an optotype, for an individual using the optometry device.

Mirrors 13, 14 are disposed at a right angle with respect to each other; in addition, mirror 13 is disposed at an angle of 45° with respect to the screen axis S. Thanks to this arrangement, the light beam produced by the screen 12 is successively reflected by mirror 13, then by mirror 14, such that it is directed towards the lens 16 along a lens axis L (the screen axis S and the lens axis L being parallel to each other).

Lens 16 is here an achromatic lens, having a focal length between 200 mm and 300 mm, for instance.

The further mirror 15 is positioned at 45° on the lens axis L, opposite mirror 14 with respect to the lens 16, such that the light beam reflected by mirror 14 along the lens axis L crosses the lens 16 and is then reflected on the further mirror 15 and directed therefrom to the individual's eye (through window 8) along an optical axis O of the optometry device.

The distance between the lens 16 and the screen 12 (along the optical path just described) is less than the focal length of the lens 16, such that the screen 12 is situated between the object focal plane of the lens 16 and the lens itself.

On the other hand, the casing 2 and the imaging module 10 are designed such that the individual's eye is situated in the image focal plane of the lens 16 (when the individual positions his head against a dedicated part of the casing 2).

The imaging module 10 is thus designed to produce a light beam B forming an image (representing an object, such as an optotype) for the individual's eyes.

In addition, mirrors 13, 14 are held on a base 18 which is slidably mounted on a support 17 of the imaging module 10 such that mirrors 13, 14 are movable along the (vertical) screen axis S. (The screen 12, the lens 16 and the further mirror 15 are fixedly attached to this support 17.)

By moving the base 18 carrying mirrors 13, 14 (for instance thanks to an electric motor 19 and associated mechanism, here a worm 11 driven by electric motor 19 and cooperating with said base 18), the length of the optical path between the screen 12 and the lens 16 can be modified.

Thanks to this, the imaging module 10 is adapted to produce the image of the object at a variable distance for the individual's eye.

The refraction unit 20 is mounted in the casing 2 so as to be interposed between the imaging module 10 and the individual's eyes. Precisely, the refraction unit 20 is located such that the light beam B produced by the imaging module 10 reaches the refraction modules 30, 30' (when the refraction modules 30, 30' are in an active position distinct from a retracted position, see below) and crosses the refraction modules 30, 30' through their respective eyepiece 35, 35'.

In the present embodiment, the refraction unit 20 is located in the vicinity of the wall 7 of the casing 2 presenting the windows 8. In particular, the refraction unit 20 is positioned such that the eyepiece 35, 35' of each refraction module 30, 30' faces a corresponding window 8 of the casing 2 such that the individual can look into the eyepieces 35, 35' of the refraction modules 30, 30' when looking into the windows 8 formed in the casing 2 (except when the refraction modules 30, 30' are in a retracted position as described below).

As already noted and clearly visible in FIGS. 3 and 4, the refraction unit 20 includes a driving module 40 on which refraction modules 30, 30' are displaceably mounted so as to adjust the position of each refraction module 30, 30' with respect to the driving module 40. The driving module 40, which will be further described below, thus makes it possible to place each refraction module 30, 30' either in front of a corresponding one of the individual's eyes or aside.

Each refraction module 30, 30' is for instance a visual compensation system as described in document WO 2015/107 303.

Such a refraction module 30, 30' is adapted to provide a variable optical correction for the individual's eye looking therethrough.

Precisely, as shown in FIG. 5, the refraction module 30 includes a lens 32 having a spherical power along the optical axis O, which spherical power is variable.

Said variable spherical power lens 32 has for instance a deformable surface (such as a deformable membrane). The shape of this surface (in particular the radius of curvature of this surface, and hence the spherical power provided by the lens) can be controlled by moving a mechanical part (such as a ring), which mechanical part may be driven by a first motor 33 of the refraction module 30.

The refraction module also includes a pair of independently rotatable lenses 34, 36 each having a cylindrical power along the optical axis O.

The two rotatable lenses 34, 36 may each be rotated by action of a second motor of the refraction module 30 and of a third motor of the refraction module 30, respectively.

The refraction module 30 includes a control unit 38 which is designed to generate controls for the first motor 33, the second motor and the third motor, respectively, such that the combination of the variable spherical power lens 32 and the two cylindrical power lenses 34, 36 provides a desired spherical correction and a desired cylindrical correction to the individual's eye, as explained in document WO 2015/107 303.

The various elements of the refraction module 30 (such as the variable spherical power lens 32, the cylindrical lenses 34, 36, the first motor 33, the second motor, the third motor and the control unit 38) are enclosed in a housing 31, which includes an eyepiece 35 on the optical axis O.

The refraction module 30' has a similar construction and is not therefore further described here.

The driving module 40 includes a base plate 41 on which two carriages 42, 42' are mounted so as to be translatable along an axis Y (this axis Y being parallel to the plane of the base plate 42).

Each carriage 42, 42' carries a corresponding gear 44, 44' which is rotatably mounted on the concerned carriage 42, 42' around an axis Z (which is perpendicular to the base plate 41 and thus to the axis Y). As visible on FIG. 3 and further explained below, a support 46, 46' of the concerned refraction module 30, 30' is mounted to the corresponding gear 44, 44'.

The driving module 40 also includes two worms 43, 45 respectively driven by a corresponding motor 47, 49 and extending along the above mentioned axis Y (i.e. along the direction of translation of carriages 42, 42' on the base plate 41). The worms 43, 45 are furthermore located on either sides of the gears 44, 44' and each worm 43, 45 engages with both gears 44, 44'.

For each worm 43, 45, the thread cooperating with one of the gear (e. g. gear 44) is however opposite to the thread cooperating with the other gear (e. g. gear 44') such that:
- when both worms 43, 45 are rotated in the same direction and at the same speed, both carriages 42, 42' are translated along the axis Y with respect to the base plate 41, but in opposite directions (the direction of translation of each carriage 42, 42' depending on the direction of rotation of the worms 43, 45);
- when both worms 43, 45 are rotated in opposite directions and at the same speed, the carriages 42, 42' do not move, but the gears 44, 44' (and hence the supports 46, 46' carrying the refraction modules 30) are rotated with respect to their carriage 42, 42' (and hence with respect to the base plate 41);
- when a single worm (e.g. worm 43) is rotated, the carriages 42, 42' are translated and the gears 44, 44' are rotated such that the supports 46, 46' of the refraction modules 30, 30' follow a movement combining translation and rotation.

Thus, by appropriate control of the rotation of the worms 43, 45 (using a control circuit driving motors 47, 49), it is possible to adjust both the position of refraction modules 30, 30' along axis Y and/or the orientation of refraction modules 30, 30' around axis Z.

For instance, the refraction modules 30, 30' can be moved along axis Y to be both positioned in front of an individual's eye (i.e. the distance between eyepieces 35, 35' of both refractions modules 30, 30' can be adjusted to the pupillary distance (PD) of the individual).

Refraction modules 30, 30' may also be (slightly) orientated around axis Z such that respective optical axes O of both refraction modules 30, 30' converge, in particular to test near vision or intermediate vision.

The refraction modules 30, 30' can also be moved to their respective lateral end position (or retracted position), where the refraction modules 30, 30' are located out of the individual's field of vision, and thus out of the light beam B (which light beam B corresponds to the image to be observed by the individual looking into the casing 2). This an retracted position is adapted for practising a subjective refraction test without any correction of the individual's vision.

In the present embodiment, the driving module 40 also includes pinions 50, 50' rotatably mounted on the base plate 41 on the same axis as a corresponding one of the gears 44, 44'.

As visible in FIG. 4, each pinion 50, 50' engages with a (single) corresponding worm 52, 52' extending along an axis parallel to axis Y and driven by a motor 54, 54'.

When worms 43, 45 are rotated by motors 47, 49 as described above, each worm 52, 52' is correspondingly rotated (by the associated motor 54, 54') such that pinions 50, 50' are translated and/or rotated in synchrony with corresponding gears 44, 44'.

However, when one of the worms 52, 52' is rotated (by the associated motor 54, 54') while worms 43, 45 are immobile, the corresponding pinion 50, 50' is rotated with respect to the associated carriage 42, 42' and gear 44, 44'.

A shaft 56, 56' extends from each pinion 50, 50' and has a threaded end engaging the support 46, 46' of a corresponding one of the refraction modules 30, 30'. In addition, an anti-rotation device (e.g. a guide between said support 46, 46' and the corresponding gear 44, 44') allows only a translation movement along axis Z between said support 46, 46' and the corresponding gear 44, 44'.

Thus, by the above-mentioned rotation of the pinion 50, 50' (driven by the associated motor 54, 54'), the position of the support 46, 46' (and hence of the corresponding refraction module 30, 30') can be adjusted along axis Z (i.e. vertically).

In the embodiments described in the present application, the illumination system 60 is located between the refraction unit 20 and the imaging module 10. In other embodiments, the illumination system could be located elsewhere in the casing 2, for instance at the bottom of the casing 2.

In the embodiment of FIG. 1, the illumination system 60 comprises two illumination modules (comprising each light sources 62 and an associated plaque 64) respectively located on both sides of the optical axis O, here closer to the further mirror 15 of the imaging module 10 than to the refraction unit 20.

The illumination system 60 comprises for instance a plurality of light sources 62 (for instance LEDs) and at least one plaque 64 of transparent plastic material placed in the vicinity of (here, in front of some of) the light sources so as to scatter and diffuse light.

The illumination system 60 is adapted to simulate ambient light for the individual. The level of this ambient light (i.e. the simulated luminosity) may be varied by varying the intensity of the light source(s), for instance by controlling (using an electronic control circuit) the intensity of the (electrical) current applied to the light source(s).

By enclosing the various elements (including the refraction unit 20, the illumination system 60 and the imaging module 10) in the casing 2, as described above, the level of light perceived by the individual's eye can be adjusted as desired; all kinds of ambient light can thus be simulated (in particular using illumination system 60), from penumbra to dazzling.

A subjective refraction test (possibly using the refraction module 30) can thus be carried out with a light level chosen by the professional, for instance to test photopic vision or mesopic vision.

Figure 6:
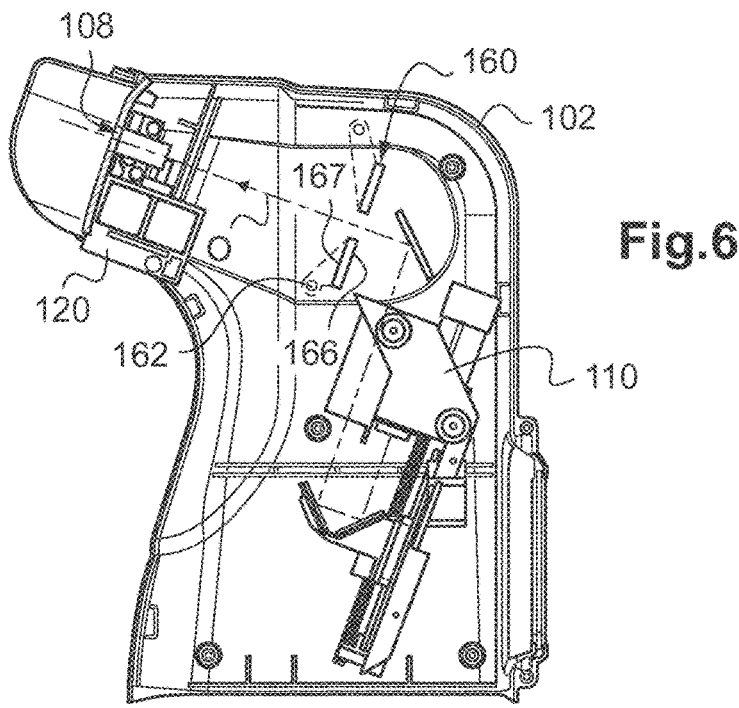
FIG. 6 shows a second embodiment of an optometry device according to the invention.

FIG. 6 shows a second embodiment of an optometry device according to the invention.

This optometry device includes a casing 102 enclosing an imaging module 110, a refraction unit 120 and an illumination system 160.

The imaging module 110 and the refraction unit 120 are identical to the imaging module 10 and the refraction unit 20 described above, respectively, and are not further described here.

A window 108 formed in the casing 102 makes it possible for an individual to look into the casing 102 (possibly through refraction modules of the refraction unit 120 if these refraction modules are not in a retracted position) and receive a light beam produced by the imaging module 110 along an optical axis O, this light beam forming an image for the individual's eyes.

The illumination system 160 comprises at least one light source 162 (here two such light sources) and at least a reflection element 166 having a surface 167 illuminated by the light source 162 and reflecting light towards the refraction unit 120 (and hence towards the individual's eyes).

The surface 167 is for instance designed (e.g. thanks to its roughness) to produce a diffuse reflection of light received from the light source 162 such that light reflected by the surface 167 is scattered inside the casing 102.

The level of the ambient light inside the casing 102 can thus be varied by varying the intensity of the light source 162 (e.g. by varying the intensity of the current applied to the light source(s) 162 using a dedicated electronic control circuit), for instance under the control of the eye care practitioner (acting on an interface adapted to transmit commands to the above mentioned electronic control circuit).

In the embodiment of FIG. 6, the illumination system 160 is located between the imaging module 110 and the refraction unit 120; here, the illumination system 160 comprises two reflecting elements 166 respectively located on both sides of the optical axis O.

Figure 7:
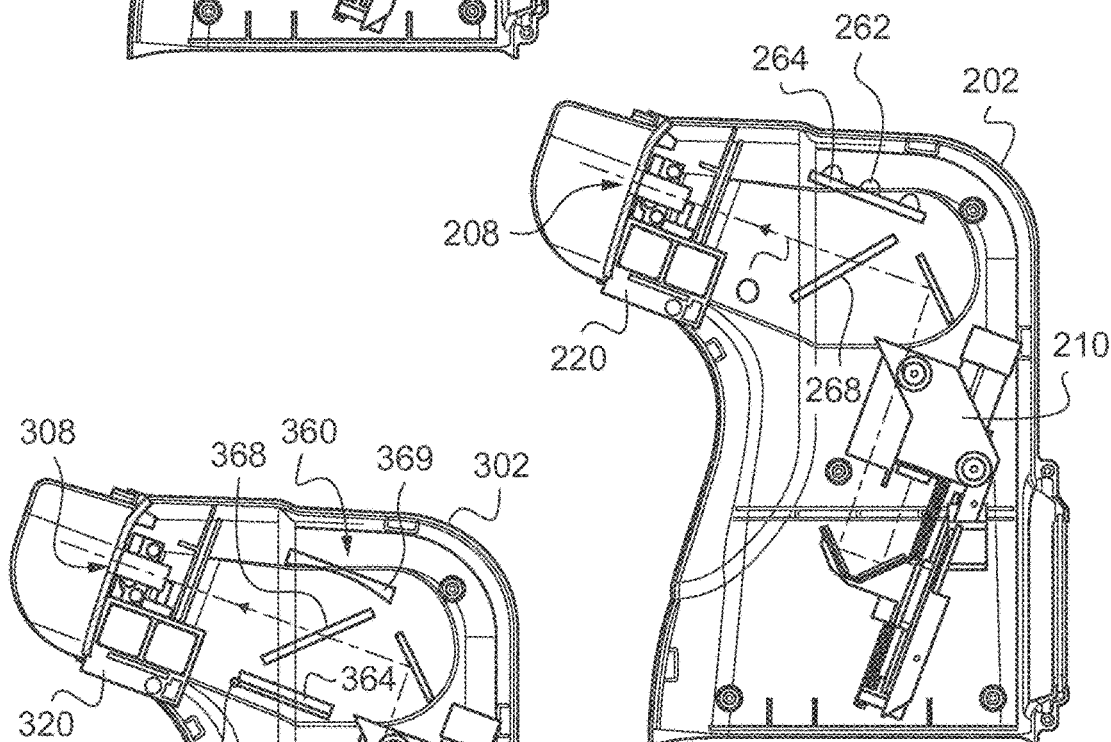
FIG. 7 shows a third embodiment of an optometry device according to the invention.

FIG. 7 shows a third embodiment of an optometry device according to the invention.

This optometry device includes a casing 202 enclosing an imaging module 210, a refraction unit 220 and an illumination system 260.

The imaging module 210 and the refraction unit 220 are identical to the imaging module 10 and the refraction unit 20 described above, respectively, and are not further described here.

A window 208 formed in the casing 202 makes it possible for an individual to look into the casing 202 (possibly through refraction modules of the refraction unit 220 if these refraction modules are not in a retracted position) and receive a light beam produced by the imaging module 110 along an optical axis O, this light beam forming an image for the individual's eyes.

The illumination system 260 comprises at least one light source 262, a plaque 264 of transparent plastic material placed in front of some of the light source(s) 262, and a beam splitter 268 facing the plaque 264 and located (on the optical axis O) between the imaging module 210 and the refraction unit 220, forming an angle of 45° with the optical axis O.

Light emitted by the light source(s) 262 is thus diffused by the plaque 264 onto the beam splitter 268, where it is (at least partially) reflected towards the refraction unit 220 (and thus towards the individual's eyes).

The individual performing a subjective refraction test using the optometry device of FIG. 7 thus observes the image produced by the imaging device 210 (owing to the light beam produced by the imaging device 210 and transmitted across the beam splitter 268) in the context of an ambient light produced by light source(s) 262.

The level of this ambient light can be varied by varying the intensity of light source(s) 262 (e.g. by varying the intensity of the current applied to the light source(s) 262 using a dedicated electronic control circuit), for instance under the control of the eye care practitioner.

This makes it possible to perform the subjective refraction test for various types of vision, such a photopic vision or mesopic vision.

Figure 8:
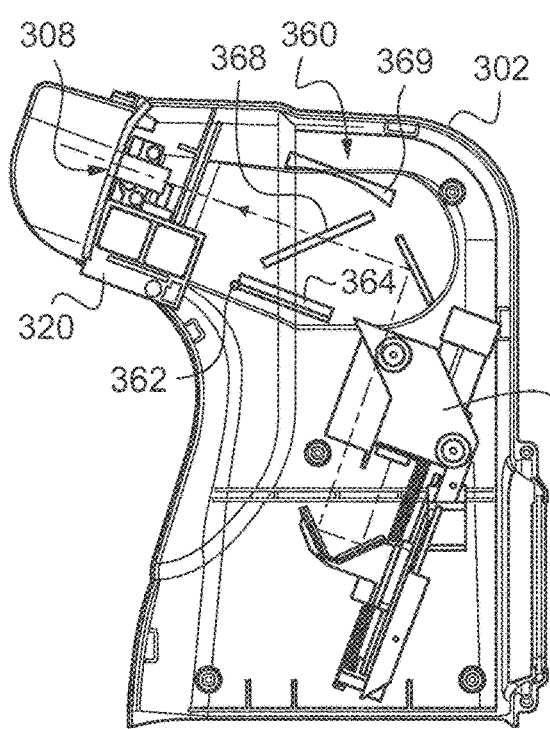
FIG. 8 shows a fourth embodiment of an optometry device according to the invention.

FIG. 8 shows a fourth embodiment of an optometry device according to the invention.

This optometry device includes a casing 302 enclosing an imaging module 310, a refraction unit 320 and an illumination system 360.

The imaging module 310 and the refraction unit 320 are identical to the imaging module 10 and the refraction unit 20 described above, respectively, and are not further described here.

A window 308 formed in the casing 302 makes it possible for an individual to look into the casing 302 (possibly through refraction modules of the refraction unit 320 if these refraction modules are not in a retracted position) and receive a light beam produced by the imaging module 310 along an optical axis O, this light beam forming an image for the individual's eyes.

The illumination system 360 comprises a screen 364 backlighted by a light source 362, a beam splitter 368 and a mirror 369 (here a concave mirror).

The screen 364, the beam splitter 368 and the mirror 369 are aligned along a direction perpendicular to the optical axis O, the beam splitter 368 being placed between the screen 365 and the mirror 369.

The beam splitter 368 is also located between the refraction unit 320 and the imaging device 310, and orientated at 45° with respect to the optical axis O.

Thanks to this construction, the light beam produced by the imaging module 310 is transmitted across the beam splitter 368 (towards the refraction unit 320 and the individual's eyes), while light emitted by the screen 364 crosses the beam splitter 368, reflects on the mirror 369 and is then eventually reflected towards the refraction unit 320 (and hence the individual's eye) by the beam splitter 368.

The optical shape of mirror 369 can be conveniently chosen so that the light emitted by the screen 364 appears as light produced at a chosen distance (for instance of at least 5 m) for the individual's eyes.

The corresponding light level can be varied by varying the intensity of the light source 362 backlighting the screen 364 (e.g. by varying the intensity of the current applied to the light source 362 using a dedicated electronic control circuit), for instance under the control of the eye care practitioner (acting on an interface adapted to transmit commands to the above mentioned electronic control circuit).

Again, this makes it possible to perform the subjective refraction test for various types of vision, such a photopic vision or mesopic vision.

The invention claimed is:

1. An optometry device for testing an individual's eye, comprising:
   a casing;
   an imaging module located in the casing and adapted to produce a light beam directed to the individual's eye;
   a refraction module adapted to provide a variable optical correction to the individual's eye looking therethrough into the casing, the refraction module including a lens with variable spherical refraction power; and
   an illumination system adapted to produce a variable ambient light level inside the casing.

2. The optometry device according to claim 1, wherein the illumination system includes at least one surface and one light source located around the imaging module.

3. An optometry device for testing an individual's eye, comprising:
   a casing;
   an imaging module located in the casing and adapted to produce a light beam directed to the individual's eye;
   a refraction module adapted to provide a variable optical correction to the individual's eye looking therethrough into the casing, the refraction module displaceably mounted between a first position in which the refraction module is crossed by the light beam, and a second position in which the refraction module is retracted out of the light beam; and
   an illumination system adapted to produce a variable ambient light level inside the casing.

4. The optometry device according to claim 3, wherein the imaging module is configured to project the light beam through an eyepiece of the refraction module when the refraction module is in the first position.

5. The optometry device according to claim 3, wherein the refraction module is mounted on a carriage having a gear cooperating with two parallel worms respectively driven by two motors.

6. The optometry device according to claim 5, wherein the refraction module is mounted on the carriage at a position adjustable along a direction perpendicular to an optical axis of the refraction module.

7. An optometry device for testing an individual's eye, comprising:
   a casing;
   an imaging module located in the casing and adapted to produce a light beam directed to the individual's eye;
   a refraction module adapted to provide a variable optical correction to the individual's eye looking therethrough into the casing, the refraction module including a pair of independently rotatable lenses with cylindrical refraction power; and
   an illumination system adapted to produce a variable ambient light level inside the casing.

8. The optometry device according to claim 1, wherein the light beam is configured to form to an optotype for the individual's eye.

9. A method of performing a test using an optometry device according to claim 1, including a step of varying said ambient light level during the test.

10. The optometry device according to claim 2, wherein the refraction module is displaceably mounted between a first position in which first position the refraction module is crossed by the light beam, and a second position in which the refraction module is retracted out of the light beam.

11. The optometry device according to claim 4, wherein the refraction module is mounted on a carriage having a gear cooperating with two parallel worms respectively driven by two motors.

12. The optometry device according to claim 3, wherein the refraction module includes a lens with variable spherical refraction power.

13. The optometry device according to claim 4, wherein the refraction module includes a lens with variable spherical refraction power.

14. The optometry device according to claim 5, wherein the refraction module includes a lens with variable spherical refraction power.

15. The optometry device according to claim 6, wherein the refraction module includes a lens with variable spherical refraction power.

16. The optometry device according to claim 2, wherein the refraction module includes a pair of independently rotatable lenses with cylindrical refraction power.

17. The optometry device according to claim 3, wherein the refraction module includes a pair of independently rotatable lenses with cylindrical refraction power.

18. The optometry device according to claim 4, wherein the refraction module includes a pair of independently rotatable lenses with cylindrical refraction power.

\* \* \* \* \*